United States Patent
Park et al.

(10) Patent No.: US 10,932,928 B2
(45) Date of Patent: Mar. 2, 2021

(54) DRUG-RELEASING BIODEGRADABLE STENT

(71) Applicant: M.I.TECH CO., LTD., Pyeongtaek-si (KR)

(72) Inventors: Hun Kuk Park, Pyeongtaek-si (KR); Jong Pil Moon, Gunpo-si (KR); Bong Seok Jang, Osan-si (KR); Ho Yun, Anyang-si (KR)

(73) Assignee: M.I.TECH CO., LTD., Pyeongtaek-si (KR)

( * ) Notice: Subject to any disclaimer, the term of this patent is extended or adjusted under 35 U.S.C. 154(b) by 30 days.

(21) Appl. No.: 16/326,053

(22) PCT Filed: Nov. 1, 2016

(86) PCT No.: PCT/KR2016/012465
§ 371 (c)(1),
(2) Date: Feb. 15, 2019

(87) PCT Pub. No.: WO2018/038318
PCT Pub. Date: Mar. 1, 2018

(65) Prior Publication Data
US 2019/0183667 A1 Jun. 20, 2019

(30) Foreign Application Priority Data
Aug. 24, 2016 (KR) .................. 10-2016-0107551

(51) Int. Cl.
*A61F 2/90* (2013.01)
*A61F 2/82* (2013.01)
(Continued)

(52) U.S. Cl.
CPC ................ *A61F 2/90* (2013.01); *A61F 2/852* (2013.01); *A61F 2/86* (2013.01); *A61L 31/14* (2013.01);
(Continued)

(58) Field of Classification Search
CPC .. A61F 2/852; A61F 2/01; A61F 2/962; A61F 2/82; A61F 2/86; A61F 2/90; A61L 31/148; A61L 31/16; A61L 2400/16
See application file for complete search history.

(56) References Cited

U.S. PATENT DOCUMENTS 5,693,085 A    12/1997  Buirge et al. .................... 623/1
7,815,673 B2 * 10/2010  Bloom .................. A61F 2/2418
                                                       623/1.15
(Continued)

FOREIGN PATENT DOCUMENTS

CN    101496754 A    8/2009
CN    104487024 A    4/2015
(Continued)

OTHER PUBLICATIONS

International Search Report dated May 22, 2017, issued to International Application No. PCT/KR2016/012465.
(Continued)

*Primary Examiner* — Dinah Baria
(74) *Attorney, Agent, or Firm* — Stein IP, LLC

(57) ABSTRACT

The present invention relates to a drug-releasing biodegradable stent. The drug-releasing biodegradable stent includes: a first stent structure configured to have a plurality of cells by means of the wire crossing pattern of a woven structure and be provided in a hollow cylindrical shape by weaving a metal wire made of a shape-memory alloy in a specific pattern on a jig; and a second stent structure formed as a 3D print that is provided to have a plurality of cells by means of the wire crossing pattern of a printed structure and also have a hollow cylindrical shape by performing 3D printing using a printing material including a biodegradable polymer and a drug, and disposed such that it covers the outer circumferential surface of the first stent structure or the outer circum- (Continued)

ferential surface thereof is covered with the first stent structure.

15 Claims, 8 Drawing Sheets

(51) Int. Cl.
| | |
|---|---|
| *A61L 31/16* | (2006.01) |
| *B29C 67/00* | (2017.01) |
| *B33Y 80/00* | (2015.01) |
| *B33Y 70/00* | (2020.01) |
| *A61L 31/14* | (2006.01) |
| *A61F 2/852* | (2013.01) |
| *A61F 2/86* | (2013.01) |

(52) U.S. Cl.
CPC ............ *A61L 31/148* (2013.01); *A61L 31/16* (2013.01); *B29C 67/00* (2013.01); *B33Y 70/00* (2014.12); *B33Y 80/00* (2014.12)

(56) References Cited

U.S. PATENT DOCUMENTS

| | | | |
|---|---|---|---|
| 8,021,418 B2* | 9/2011 | Gerberding | ............. A61L 31/10 623/1.34 |
| 2005/0004653 A1 | 1/2005 | Gerberding et al. | ........ 623/1.13 |
| 2006/0147612 A1 | 7/2006 | Da Rocha Loures | ....... 427/2.25 |
| 2009/0192588 A1 | 7/2009 | Shin et al. | ................... 623/1.15 |
| 2011/0060398 A1* | 3/2011 | Tupil | ........................ A61F 2/07 623/1.15 |
| 2013/0131778 A1 | 5/2013 | Igaki et al. | ................. 623/1.12 |
| 2013/0331927 A1 | 12/2013 | Zheng et al. | ................ 623/1.19 |
| 2017/0181872 A1 | 6/2017 | Kwon et al. | ........................ 2/82 |
| 2018/0117219 A1* | 5/2018 | Yang | ....................... A61L 31/16 |

FOREIGN PATENT DOCUMENTS

| | | |
|---|---|---|
| EP | 2 085 050 A1 | 8/2009 |
| JP | 2006-527630 A | 12/2006 |
| WO | WO 2012/011269 A1 | 1/2012 |
| WO | WO 2013/138789 A1 | 9/2013 |
| WO | WO 2015/194759 A1 | 12/2015 |
| WO | WO 2016/118669 A1 | 7/2016 |

OTHER PUBLICATIONS

Chinese Office Action dated Apr. 17, 2020, issued to Chinese Application No. 201680088648.6.
European Search Report dated Feb. 25, 2020, issued to European Application No. 16914297.3.
Second Chinese Office Action dated Sep. 21, 2020, issued to Chinese Application No. 201680088648.6.

* cited by examiner (a)

(b)

(a)

(b)

(a)

(b)

DRUG-RELEASING BIODEGRADABLE STENT

CROSS-REFERENCE TO RELATED APPLICATIONS

This application is a national stage of International Application No. PCT/KR2016/012465, filed Nov. 1, 2016, which claims the benefit of priority to Korean Application No. 10-2016-0107551, filed Aug. 24, 2016, in the Korean Intellectual Property Office, the disclosures of which are incorporated herein in their entireties by reference.

TECHNICAL FIELD

The present invention relates to a drug-releasing biodegradable stent.

BACKGROUND ART

Generally, a stent is placed to be located in a lumen, such as a lesion where a stenosis has occurred, and performs structural expansion at a placement location by means of the shape memory feature of a metal wire or the assistance of a separate expansion member. Accordingly, the stent functions to restore the diameter of the lumen narrowed due to the occurrence of the stenosis while maintaining a predetermined shape inside the lumen for a long period of time, and also functions to ensure a movement path in order to enable materials to be smoothly moved through the expanded lumen.

Such stents are basically intended to restore the diameters of lumens. Recently, there have been developed stents each configured such that a separate coating film is disposed on the outer circumferential surface of a stent or a coating layer is formed on the surface of a wire constituting the framework of a stent and then the stent placed in a lumen releases a drug included in the coating film or coating layer.

The stents release drugs while restoring the diameters of lumens, and thus continuous drug treatment is performed on the lesion generation regions of lumens, where the stents are placed, for predetermined periods of time, thereby enabling an effect, such as an anticancer or antibacterial effect, to be provided.

In connection with this, a related art document regarding a conventional technology that is provided to store a drug on a stent wire structure and to release the drug after a predetermined period of time has elapsed from the placement of a stent includes Korean Patent No. 10-1467102 entitled "Drug-storing Multilayer Structure and Drug-releasing Stent Including the Same" (hereinafter referred to as the 'related art').

However, conventional drug-releasing stents including the conventional technology employ a method of additionally applying a coating film containing a separate drug by performing a coating process on a metal wire-based stent structure. Therefore, these stents have problems in that it is difficult to accurately design a substantial coating region to be provided to apply a drug to a lesion through the release of the drug and in that the quantity, speed and release time of the drug to be released are somewhat insufficient for the drug to act on a lesion and provide a sufficient effect to the lesion.

Moreover, although the conventional drug-releasing stent in which a biodegradable polymer forms a main wire framework provides an appropriate quantity of drug to a lesion, it has problems in that it does not sufficiently provide the effect of restoring the diameter of a lumen, which is provided by a metal wire-based stent structure, and in that it is easily removed from a placement location because the property of preventing movement is not sufficiently provided.

DISCLOSURE

Technical Problem

The present invention has been conceived to overcome the above-described problems, and an object of the present invention is to provide a stent that basically and sufficiently provides the property of expanding a lumen and the property of preventing movement at a stent placement location and that enables a drug release region to be set through accurate design in connection with the provision of a lesion treatment effect through the release of a drug and also enables a drug-release pattern, such as the quantity, speed and release time of drug to be released, to be based on the structure of the stent, thereby enabling the provision of an effective treatment effect.

Technical Solution

In order to accomplish the above object, according to a first embodiment of the present invention, there is provided a drug-releasing biodegradable stent, including: a first stent structure configured to have a plurality of cells by means of the wire crossing pattern of a woven structure by weaving a metal wire made of a shape-memory alloy in a specific pattern on a jig and be provided in a hollow cylindrical shape; and a second stent structure formed as a 3D print that is provided to have a plurality of cells by means of the wire crossing pattern of a printed structure by performing 3D printing using a printing material including a biodegradable polymer and a drug and also have a hollow cylindrical shape, and disposed such that it covers the outer circumferential surface of the first stent structure or the outer circumferential surface thereof is covered with the first stent structure.

In this case, a coating layer containing a drug may be formed on the surface of the second stent structure through a surface coating process using a coating mixture, in which a biodegradable polymer and a drug are mixed together, after 3D printing.

Additionally, the types and/or composition ratios of the biodegradable polymers may differ from each other so that the biodegradable polymer in the printing material used to prepare the second stent structure through 3D printing has a longer biodegradation period than the biodegradable polymer in the coating mixture used to prepare the coating layer placed and applied onto the surface of the second stent structure.

Furthermore, the drug in the printing material used to prepare the second stent structure through 3D printing and the drug in the coating mixture used to prepare the coating layer placed and applied onto the surface of the second stent structure may be provided as the same type of drugs.

Moreover, the first stent structure may include: a first body portion formed in a hollow cylindrical shape; a first expanded portion formed at one end of the first body portion to have a larger diameter than the first body portion; and a second expanded portion formed at the other end of the first body portion to have a larger diameter than the first body portion; and the second stent structure may be provided to have the same or a shorter length than the first body portion, and may be disposed such that it covers the outer circumferential surface of the first body portion or the outer circumferential surface thereof is covered with the body portion.

In this case, the drug-releasing biodegradable stent may further include a plurality of radiopaque markers disposed at the plurality of portions of the first stent structure in order to ensure the visibility of a stent placed in a human body, and at least two of the plurality of radiopaque markers which are disposed at both ends the body portion may be each disposed to fasten and connect both ends of the second stent structure to the body portion.

In order to accomplish the above object, according to a second embodiment of the present invention, there is provided a drug-releasing biodegradable stent, including: a first stent structure configured to have a plurality of cells by means of the wire crossing pattern of a woven structure by weaving a metal wire made of a shape-memory alloy in a specific pattern on a jig and be provided in a hollow cylindrical shape; a second stent structure formed as a 3D print that is provided to have a plurality of cells by means of the wire crossing pattern of a printed structure by performing 3D printing using a printing material including a biodegradable polymer and a drug and also have a hollow cylindrical shape; and a third stent structure configured to have a plurality of cells by means of the wire crossing pattern of a woven structure by weaving a metal wire made of a shape-memory alloy in a specific pattern on a jig and be provided in a hollow cylindrical shape, and disposed such that it covers the outer circumferential surface of the first stent structure or the outer circumferential surface thereof is covered with the first stent structure; wherein the second stent structure is inserted into and disposed in a space between the first stent structure and the third stent structure.

In this case, a coating layer containing a drug may be formed on the surface of the second stent structure through a surface coating process using a coating mixture, in which a biodegradable polymer and a drug are mixed together, after 3D printing.

Additionally, the types and/or composition ratios of the biodegradable polymers may differ from each other so that the biodegradable polymer in the printing material used to prepare the second stent structure through 3D printing has a longer biodegradation period than the biodegradable polymer in the coating mixture used to prepare the coating layer placed and applied onto the surface of the second stent structure.

Furthermore, the drug in the printing material used to prepare the second stent structure through 3D printing and the drug in the coating mixture used to prepare the coating layer placed and applied onto the surface of the second stent structure may be provided as the same type of drugs.

Moreover, the first stent structure may include: a first body portion formed in a hollow cylindrical shape; a first expanded portion formed at one end of the first body portion to have a larger diameter than the first body portion; and a second expanded portion formed at the other end of the first body portion to have a larger diameter than the first body portion; the third stent structure may include: a second body portion formed in a hollow cylindrical shape; a third expanded portion formed at one end of the second body portion to have a larger diameter than the second body portion; and a fourth expanded portion formed at the other end of the second body portion to have a larger diameter than the second body portion; and the second stent structure may be provided to have the same or a shorter length than the first body portion and the second body portion, and may be inserted and disposed between the first body portion and the second body portion.

In this case, at least one coupling portion configured to integrate the first expanded portion and the third expanded portion with each other or integrate the second expanded portion and the fourth expanded portion with each other may be provided on each side of the first stent structure and the third stent structure between which the second stent structure is inserted and disposed.

Advantageous Effects

According to the present invention, the following effects are achieved:

First, the metal wire-based first stent structure and the biodegradable polymer-based second stent structure provided through 3D printing are combined into the single overall stent, and thus both the function of restoring the luminal diameter of a lesion generation region through the expansion of the first stent structure and the function of treating a lesion in the lesion generation region through the drug release of the second stent structure may be simultaneously provided.

Second, the second stent structure used to release the drug is prepared by performing 3D printing using the printing material including the biodegradable polymer and the drug, and thus the drug is uniformly distributed and carried inside the second stent structure corresponding to a 3D print, thereby effectively providing a lesion treatment effect based on the release of the drug.

Third, the drug-releasing coating film is additionally formed on the outside of the second stent structure, prepared by performing 3D printing, by performing a coating process on the second stent structure, and thus a larger quantity of drug may be provided. Additionally, drugs may be sequentially released at a time interval by making the biodegradation period of the biodegradable polymer constituting part of the second stent structure and the biodegradation period of the biodegradable polymer constituting part of the coating film different from each other.

Fourth, most preferably, the length of the second stent structure is provided to be same as or shorter than the length of the center body of the metal wire-based first stent structure or third stent structure that substantially performs the function of restoring a luminal diameter, and thus there may be minimized an unnecessary region where the drug is released in the expanded portions provided to prevent the stent from being moved and does not appropriately act on a lesion.

MODE FOR INVENTION

Figure 1:
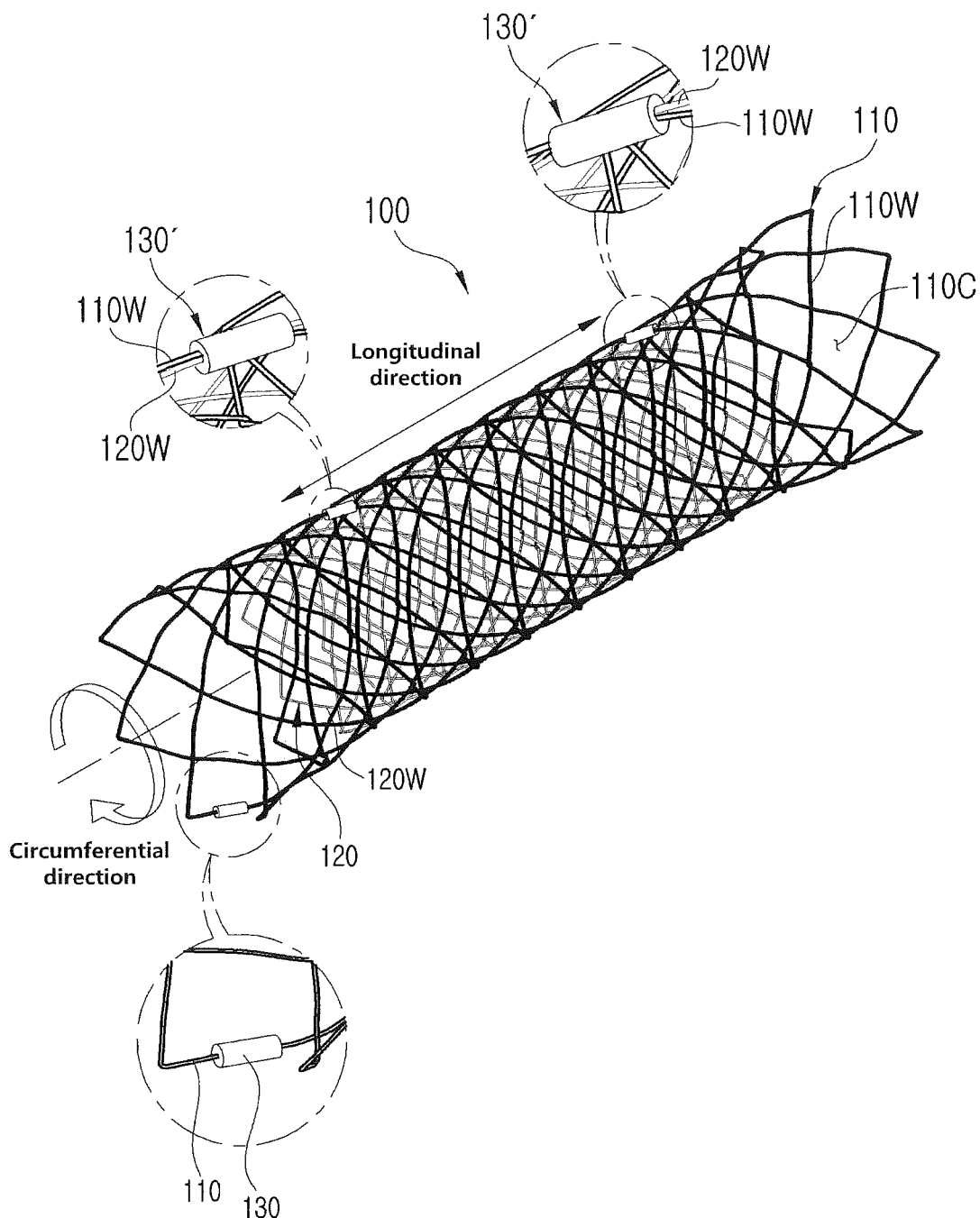
FIG. 1 is a perspective view showing the structure of a drug-releasing biodegradable stent according to a first embodiment of the present invention.

Preferred embodiments of the present invention will be described in greater detail with reference to the accompanying drawings, but descriptions of well-known technical parts will be omitted or abridged for brevity of description.

<Description of the Components and Structure of a Drug-Releasing Biodegradable Stent According to a First Embodiment>

Referring to FIGS. 1 to 4, a drug-releasing biodegradable stent 100 according to a first embodiment of the present invention includes: a first stent structure 110; a second stent structure 120; and radiopaque markers 130.

The first stent structure 110 corresponds to the first member of the luminal diameter restoration stent that is provided in a hollow cylindrical shape having a plurality of cells 110C by means of the wire crossing pattern of a woven structure by being woven in a specific pattern on a jig through the upward and downward bending of a metal wire 110W made of a shape-memory alloy.

The above-described first stent structure 110 may be prepared by at least one metal wire 110W. When a woven structure is formed using two or more metal wires 110W, the parts of a body structure prepared by the respective wires are divided into a first part and a second part. In this case, it is preferred that these parts are connected to each other via a mutually woven structure.

In this case, the first stent structure 110 is provided as a first body portion 111, a first expanded portion 112, and a second expanded portion 113 according to their location in an overall structure and the level of their diameter.

First, the first body portion 111 is the central body portion of the stent that substantially performs the function of restoring a luminal diameter at a stent placement location through the expansion of the first stent structure 110. The first body portion 111 is formed in a hollow cylindrical shape.

Next, the first expanded portion 112 is one end wing portion of the stent that extends from one end of the first body portion 111, that has a larger diameter than the first body portion 111, and that provides the property of preventing the stent from being removed and moved when the stent is placed.

Finally, the second expanded portion 113 is the other end wing portion of the stent that extends from the other end of the first body portion 111, that has a larger diameter than the first body portion 111, and that provides the property of preventing the stent from being removed and moved when the stent is placed.

The second stent structure 120 is a 3D print that is provided to have a plurality of cells 120C by means of the wire (120W) crossing pattern of a printed structure and to also have a hollow cylindrical shape by performing 3D printing using a printing material including a biodegradable polymer M1 and a drug D1. The second stent structure 120 is the second member of the stent for the provision of a treatment effect to a lesion through the release of a drug.

Through the above process, as a product of 3D printing, the overall framework of the second stent structure 120 is formed based on the biodegradable polymer, and the drug included in the printing material is uniformly distributed throughout the inside of the second stent structure 120.

First, the biodegradable polymer M1 that may be included in the printing material may be provided as any one or combination of polyethylene, polyester, polypropylene, polyvinyl chloride, expanded poly(tetrafluoroethylene) (ePTFE), polyethylene naphthalate, polybutylene naphthalate, polytrimethylene naphthalate, trimethylene diol naphthalate, polytetrafluoroethylene, polyurethane, polyurea, silicone, polyamide, polyimide, polycarbonate, polyaldehyde, polyether ether ketone, natural rubber, fluorinated ethylene propylene such as polyether, fluorinated ethylene propylene, polyvinyl acetate, polystyrene, poly(ethylene terephthalate), naphthalene, fully or partially halogenated polyether such as a dicarboxylate derivative, polyvinyl alcohol, polyethylene glycol, polylactide, polyglycolide, polyethylene oxide, polydioxanone, polycaprolactone, polyphosphazene, polyanhydride, polyamino acid, cellulose acetate butyrate, cellulose triacetate, polyacrylate, polyacrylamide, polysiloxane, polyvinylpyrrolidone, Dacron, and the copolymers thereof.

More specifically, the biodegradable polymer M1 may be a polyester-based copolymer, a styrene-butadiene copolymer, a silicon urethane copolymer, or the like.

Furthermore, in an embodiment, the biodegradable polymer M1 may be provided as any one or combination of poly(L-lactide) (PLLA), poly(D,L-lactide) (PLA), poly(glycolide) (GPA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), polycaprolactone (PCL), polyhydroxybutyrate (PHBT), poly (phosphazene) poly(D,L-lactide-co-caprolactone) (PLA/PCL), poly(glycolide-co-caprolactone) (PGA/PCL), poly(phosphate ester), and the copolymers thereof.

Next, the drug D1 that may be included in the printing material may be provided as any one or combination of anticancer agents (paclitaxel, doxorubicin, gemcitabin, 5-FU, abraxane, vinblastin, sorafenib, cetuximab, imatinib, gefitinib, elotinib, sunitinib, trastuzumab, capecitabine, etc.), antibiotic agents (cefotaxime, vancomycin, tetracycline, betalactam antibiotics, polyamicin, sulfameric antibiotics, pyrimethamine, rifampin, quinolone, aminoglycoside, etc.), immunosuppressants (all limus-based immunosuppressants, such as sirolimus, zotarolimus, everolimus, etc.), and antiplatelet agents (cilostazol).

Additionally, the drug D is not limited thereto, and may be provided in various manners. For example, the drug D1 may be provided as any one or combination of adrenergic agonists, adrenocortical steroids, adrenocorticotropic agents, alcohol inhibitors, aldosterone antagonists, amino acids and proteins, ammonia detoxicants, anabolic agents, analeptic agents, analgesics, androgenic agents, anesthetic agents, non-appetizing compounds, neurogenic anorexia patient agents, antagonists, anterior pituitary actuators and inhibitors, anthelmintics, anti-adrenergic agents, antiallergic drugs, anti-amebic agents, anti-androgenic agents, antianemic agents, anti-anginal agents, anxiolytic agents, anti-arthritic agents, anti-asthmatic agents, anti-atherosclerotic agents, antimicrobial agents, anticholelithic agents, anti-gallstone agents, anticholinergics, anticoagulants, anticoccidal agents, anticonvulsants, antidepressants, antidiabetics, diuretics, antidotes, anti-dyskinetic agents, antiemetic drugs, antiepileptic drugs, antiestrogens, anti-fibrinolytic agents, antifungal agents, anti-glaucoma agents, hemophilia agents, anticoagulants, antihemorrhagics, antihistamines, antihyperlipidemic agents, antihyperlipoproteinemics, antihypertensives, antihypotensives, anti-inflammatory agents, antibiotic agents, anti-migraine agents, cell division inhibitors, antifungal agents, anti-neoplastic agents, anti-cancer supplementary potentiating agents, anti-neutropenic agents, anti-obsessive agents, anti-parasitic agents, anti-parkinsonian agents, anti-lung cystic agents, anti-proliferative agents, anti-prostatic hyperplasia drugs, antiprotozoal agents, antipruritic agents, antipsoriatics, antipsychotic drugs, antirheumatic agents, antischistosomal agents, antiseborrhoeic agent, anticonvulsants, anti-thrombotic agents, cough suppressants, anti-ulcer agents, anti-urolith agents, antiviral agents, bone resorption inhibitors, bronchodilators, carbonic anhydrase inhibitors, cardiac depressants, cardioprotective agents, cardiac stimulants, cardiovascular agents, choleretic agents, cholinergic agents, cholinergic promoters, corin esterase inactivators, anticoccidial agents, sedatives, diagnostic assistants, diuretics, dopamine agents, ectoparasitesides, vomitogenic agents, enzyme inhibitors, estrogenic hormones, fibrous agents, free oxygen radical scavengers, gastrointestinal motility agents, glucocorticoids, gonadotropic sources, hemostatic agents, histamine H2 receptor antagonists, hormones, hypocholesterolemic agents, hypoglycemic agents, hypolipemiant drugs, hypotensive agents, hmgcoa reductase inhibitors, immunizing dose agents, immunomodulators, immunomodulator substances, keratolytic agents, LHRH antagonists, luteolycin agents, mucopolysaccharide hydrolyzates, mucosal barriers, mydriatics, nasal decongestants, neuroleptic agents, neuromuscular blockers, neuroprotective agents, NMDA antagonists, non-hormonal sterol derivatives, oxytocic agents, and plasminogen activators.

The printing material that may be prepared via one of the above-described various combinations may be practiced in such a manner that the type and composition content ratio of the biodegradable polymer used to determine the composition content ratio and drug release period of the drug may be changed through design in various manners according to the purpose of providing a drug-based treatment effect to a lesion via the second stent structure 120.

The printing material prepared as described above is prepared to include only the biodegradable polymer and the drug, and is applied to a Fused Deposition Modeling (FDM)-type 3D printer. It is most preferred that a spray location is continuously changed in response to the rotation of a build plate in a process, in which the printing material melted by the application of heat is sprayed via a nozzle and solidified on the build plate, by providing the build plate in a cylindrical form and then rotating the build plate around an axis during 3D printing, thereby enabling the hollow cylindrical second stent structure 120 to be provided.

However, the provision of the hollow cylindrical second stent structure 120 is not limited thereto. The hollow cylindrical second stent structure 120 may be printed by performing 3D printing via a 3D printer, to which Digital Light Processing (DLP), Stereolithography Apparatus (SLA), Selective Laser Sintering (SLS), or Poly-Jet is applied, by using a printing material including a thermal or UV polymerization monomer and a thermal or UV polymerization initiator in addition to the biodegradable polymer and the drug.

The drug D1 is distributed throughout the inside of the overall structure of the above-described 3D printing-based second stent structure 120 at an appropriate level, and the design of the compositional content levels and type of the printing material may be changed in various manners. Accordingly, the corresponding drug-releasing stent structure may be easily provided according to a stent placement region and purpose.

In other words, when the second stent structure 120 having biodegradability and drug releasability is provided through 3D printing, a designer may easily control and provide a required drug for release, a drug release pattern, and dimensions, such as diameter and length, according to a stent placement region and purpose, and also the drug may be distributed throughout the overall structure of the stent in a balanced manner.

Furthermore, in terms of the overall structure of the drug-releasing biodegradable stent 100, the degree of the distribution of a metal wire, such as the first stent structure 110, is minimized via the second stent structure 120, thereby further improving the biocompatibility of the stent that is placed within a human body.

The first stent structure 110 and the second stent structure 120 are connected to each other according to a first connection configuration in such a manner that the outer circumferential surface of the second stent structure 120 is covered with the first stent structure 110, as shown in FIGS. 3(a) and 1. Accordingly, the drug D1 may be released from the inside of the first stent structure 110 due to the biodegradation of the biodegradable polymer M1 that forms part of the wire 120W of the second stent structure 120.

Furthermore, a first stent structure 110' and a second stent structure 120' are connected to each other according to a second connection configuration in such a manner that the outer circumferential surface of the first stent structure 110 is covered with the second stent structure 120, as shown in FIG. 3(b). Accordingly, a drug D1 may be released from the outside of the first stent structure 110 due to the biodegradation of a biodegradable polymer M1 that forms part of the wire 120W of the second stent structure 120.

More specifically, it is preferred that the second stent structure 120 is provided to have the same or a shorter length 120D as and than the first body portion 111 and is disposed such that it covers the outer circumferential surface of the first body portion 111 or the outer circumferential surface thereof is covered with the body portion 111.

Figure 2:
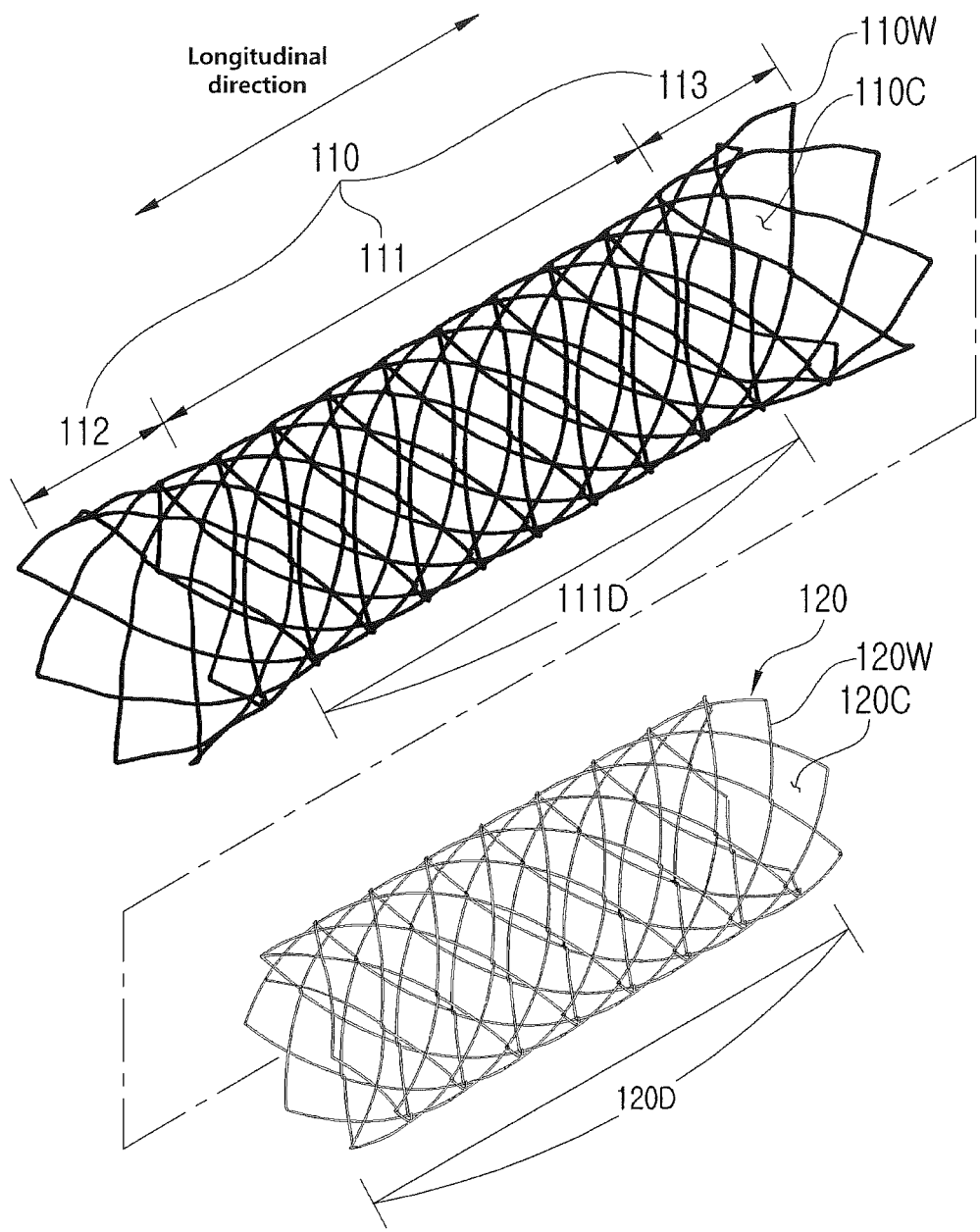
FIG. 2 is an exploded perspective view showing the structure of the drug-releasing biodegradable stent according to the first embodiment of the present invention.
Figure 3:
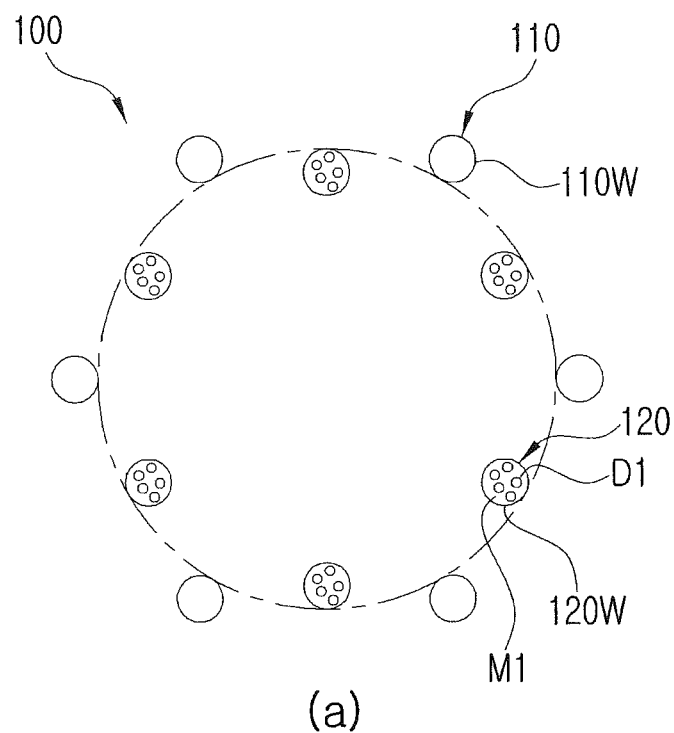
FIG. 3 show sectional views illustrating sectional structures based on mutual connection configurations between the stent structures of the drug-releasing biodegradable stent according to the first embodiment of the present invention.
Figure 3:
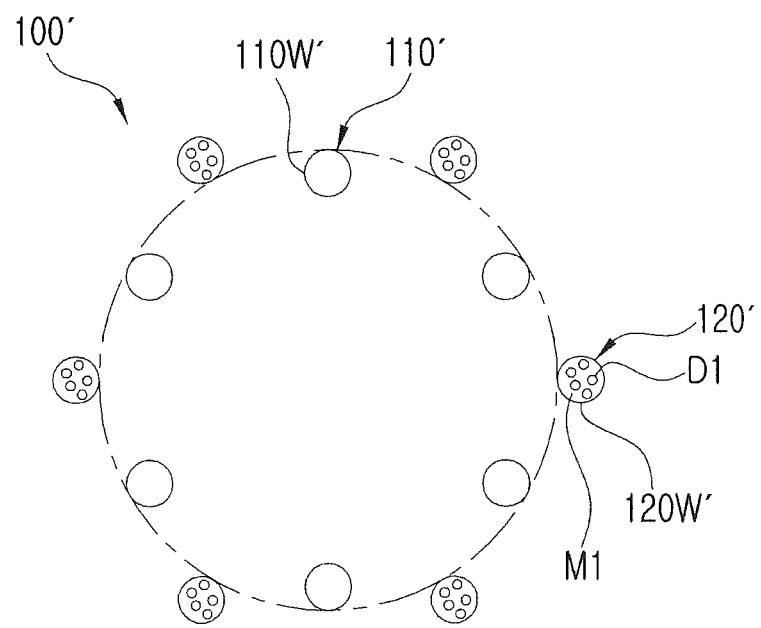

In other words, the length 120D of the second stent structure 120 is provided to be the same as or slightly shorter than the length 111D of the first body portion 111, as shown in FIG. 2.

The reason for this is to enable the drug to be effectively applied to a lesion without being applied to an unnecessary region by taking into account the fact that the first body portion 111 configured to substantially perform the function of restoring a luminal diameter narrowed due to the occurrence of the lesion comes into direct contact with the lesion.

In other words, the length 120D of the second stent structure 120 is provided to be the same as or slightly shorter than the length 111D of the first body portion 111, and the second stent structure 120 is disposed to correspond to the first body portion 111 and located near a lesion when the stent is placed.

Meanwhile, the second stent structures 420 and 420' provided through 3D printing may be additionally subjected to a separate coating process.

A coating layer 425 or 425' containing a drug may be formed on the surface of each of the second stent structures 420 and 420' through a surface coating process using a coating mixture of a biodegradable polymer M2 and a drug D2 after 3D printing.

Figure 4:
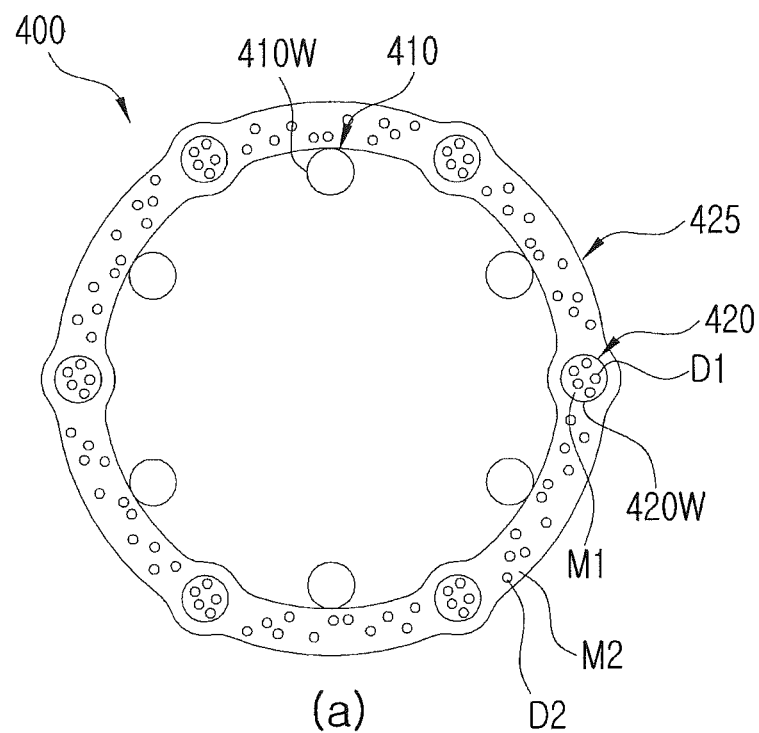
FIG. 4 shows sectional views illustrating sectional structures based on mutual connection configurations between stent structures in the state in which the second stent structure of the drug-releasing biodegradable stent according to the first embodiment of the present invention has been subjected to a coating process.
Figure 4:
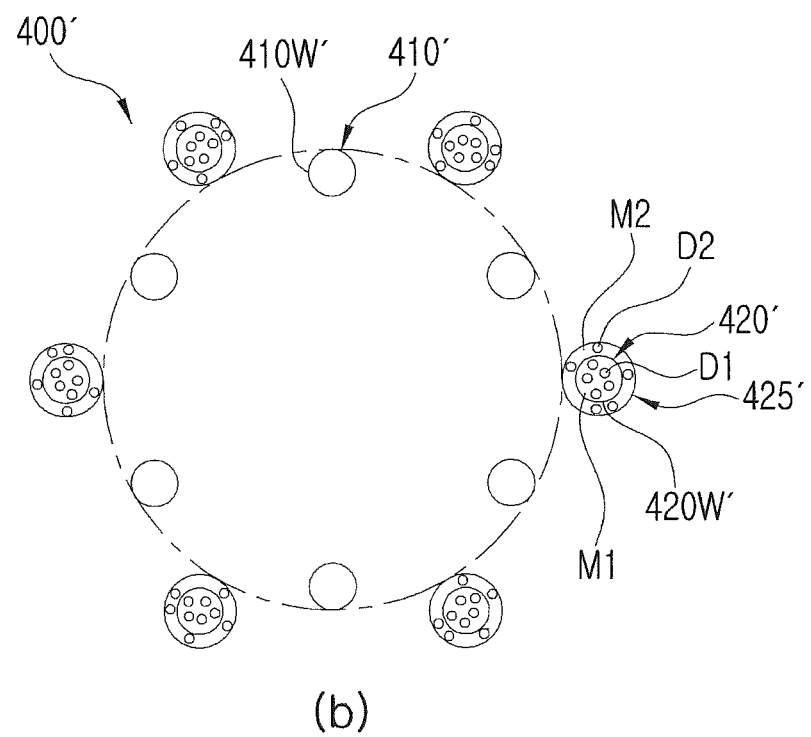

In this case, coating layer formation configurations may be divided into two types, as shown in FIG. 4. First, the sectional structure of a drug-releasing biodegradable stent 400 having a first coating configuration is as shown in FIG. 4(a).

The film-shaped coating layer 425 is formed throughout the overall second stent structure 420 of the drug-releasing biodegradable stent 400 having a first coating configuration through the spraying of a coating mixture or a deposition process in a coating mixture after 3D printing, as shown in FIG. 4(a).

Furthermore, as a result, the cell structure of the second stent structure 420 is blocked by the coating layer 425 constituting a film and forms a tubular shape as a whole, and the first stent structure 410 is disposed inside or outside the film-shaped coating layer 425 of the second stent structure 420.

The coating layer 425' is placed and applied onto the outside of the surface of a wire structure 420W constituting the framework of the second stent structure 420' of the drug-releasing biodegradable stent 400' having a second coating configuration through the spraying of a coating mixture or a deposition process in a coating mixture after 3D printing, as shown in FIG. 4(b).

Furthermore, as a result, the cell structure of the second stent structure 420' is merely narrowed but is not blocked by the coating layer 425', and the first stent structure 410' is disposed inside or outside the second stent structure 420' around which the coating layer 425' is formed on the wire structure.

The coating layers 425 and 425', which may be provided in various configurations, as described above, are provided using the coating mixture in which the biodegradable polymer M2 and the drug D2 are mixed together. The embodiments of the biodegradable polymer M2 and the drug D2 used in the coating mixture are the same as the embodiments of the biodegradable polymer M1 and the drug D1 used in the above-described a printing material.

The coating layers 425 and 425' additionally formed in the second stent structures 420 and 420' are intended to allow the drug D2 to be released due to the biodegradation of the biodegradable polymer M2 of the coating layers 425 and 425' before the release of the drug D1 attributable to the biodegradation of the biodegradable polymer M1 of the second stent structures 420 and 420'.

For this purpose, it is preferable to design biodegradable polymers so that the types and/or composition ratios thereof differ from each other so that the biodegradable polymer M1 in the printing material used to prepare the second stent structures 420 and 420' through 3D printing has a longer biodegradation period than the biodegradable polymer M2 in the coating mixture used to prepare the coating layers 425 and 425' placed and applied onto the surface of the second stent structure 420 or 420'.

Furthermore, it is preferred that the drug D1 in the printing material used to prepare the second stent structures 420 and 420' through 3D printing and the drug in the coating mixture used to prepare the coating layers 425 and 425' placed and applied onto the surface of the second stent structure 420 or 420' may be provided as the same type of drugs.

As a result, this enables the drug to be primarily applied to a lesion through the release of the drug D2 attributable to the biodegradation of the biodegradable polymer M2 of the coating layers 425 and 425', and then enables the drug D1 to be secondarily released due to the biodegradation of the biodegradable polymer M1 of the second stent structures 420 and 420' after a predetermined time.

In an embodiment, an additional design may be made such that the coating layer 425' is placed and formed on each of the second stent structures 420 and 420' in a plurality of layers and the drug is released a plurality of times at time intervals.

Furthermore, in an embodiment, the drug D1 in the printing material used to prepare the second stent structures 420 and 420' through 3D printing and the drug in the coating mixture used to prepare the coating layers 425 and 425' placed and applied onto the surface of the second stent structure 420 or 420' may be provided as different types of drugs so that two or more types of drugs may be provided to a lesion in such a manner that a first drug is primarily released and a second drug different from the first drug is secondarily released.

The radiopaque markers 130 are disposed in the plurality of portions of the first wire structure 110 in order to ensure the visibility of the drug-releasing biodegradable stent 100 disposed within a human body, as shown in FIG. 1.

In this case, the plurality of radiopaque markers 130 are a type of markers that are used to determine the location of the drug-releasing biodegradable stent 100 within a human body from the outside through inspection using radioactive rays, such as X rays. Although the radiopaque markers 130 perform a location marker function as their main function, some of the radiopaque markers 130 function as combined connector and radiopaque markers 130', as shown in the enlarged portions of FIG. 1.

In other words, at least two radiopaque markers 130' of the plurality of radiopaque markers 130 disposed at both ends of the first body portion 111 of the first stent structure 110 are disposed to connect both ends of the second stent structure 120 to the both end portions of the outer circumferential surface of the first body portion 111, as shown in the enlarged portions of FIG. 1, and provide both a location marker function and the function of fixing locations through connection between the second stent structure 120 and the first stent structure 110.

Additionally, in an embodiment, the drug-releasing biodegradable stent 100 further includes a separate film (not shown) that is placed inside or outside the first stent structure 110.

In this case, although the film may be selected from among Teflon, silicone, polytetrafluoroethylene (PTFE), polyurethane, polyester, polypropylene, polyethylene, polyolefin, high density polyethylene (HDPE), and expanded-polytetrafluoroethylene (ePTFE), it may be selected within the range of known materials used for a film without any particular limitation.

<Description of the Components and Structure of a Drug-Releasing Biodegradable Stent According to a Second Embodiment>

Referring to FIGS. 5 to 8, a drug-releasing biodegradable stent 500 according to a second embodiment of the present invention includes: a first stent structure 510; a second stent structure 520; a third stent structure 530; and radiopaque markers 540.

The second embodiment of the present invention will be described with a focus on the differences between the second embodiment and the first embodiment, and redundant descriptions will be abridged or omitted.

In this case, the constitutive features of the first stent structure 510, second stent structure 520, and radiopaque markers 540 of the drug-releasing biodegradable stent 500 according to the second embodiment of the present invention correspond to the descriptions of the constitutive features of the first stent structure 510, second stent structure 520, and radiopaque markers 540 of the drug-releasing biodegradable stent 500 according to the first embodiment of the present invention in the same manner, and thus redundant descriptions thereof will be omitted.

First, the drug-releasing biodegradable stent 500 according to the second embodiment further includes one more metal wire-based stent structure, such as the first stent structure 510. The woven structure and dimensions of the third stent structure 530 corresponding to the above metal wire-based stent structure may be the same as or different from those of the first stent structure 510.

More specifically, the third stent structure 530 has a plurality of cells by means of the wire crossing pattern of a woven structure and is provided in a hollow cylindrical shape by weaving a metal wire 530W made of shape-memory alloy material in a specific pattern on a jig.

Accordingly, the first stent structure 510 corresponds to the first member of a luminal diameter restoration stent that is provided in a hollow cylindrical shape having a plurality of cells 510C by means of the wire crossing pattern of a woven structure by being woven in a specific pattern on a jig through the upward and downward bending of a metal wire 510W made of a shape-memory alloy, and the third stent structure 530 corresponds to the second member of the luminal diameter restoration stent that is provided in a hollow cylindrical shape having a plurality of cells 530C by means of the wire crossing pattern of a woven structure by being woven in a specific pattern on a jig through the upward and downward bending of the metal wire 530W made of a shape-memory alloy.

Furthermore, the second stent structure 520 is a 3D print that is provided to have a plurality of cells 520C by means of the wire (520W) crossing pattern of a printed structure and to have a hollow cylindrical shape by performing 3D printing using a printing material including a biodegradable polymer M1 and a drug D1. The second stent structure 520 is the third member of the stent for the provision of a treatment effect to a lesion through the release of a drug.

Additionally, coating layers 525' and 525" containing a drug may be formed on the surface of the second stent structure 520' or 520" through a surface coating process using a coating mixture, in which the biodegradable polymer M2 and the drug D2 are mixed together, after 3D printing, as in the above-described first embodiment.

Figure 7:
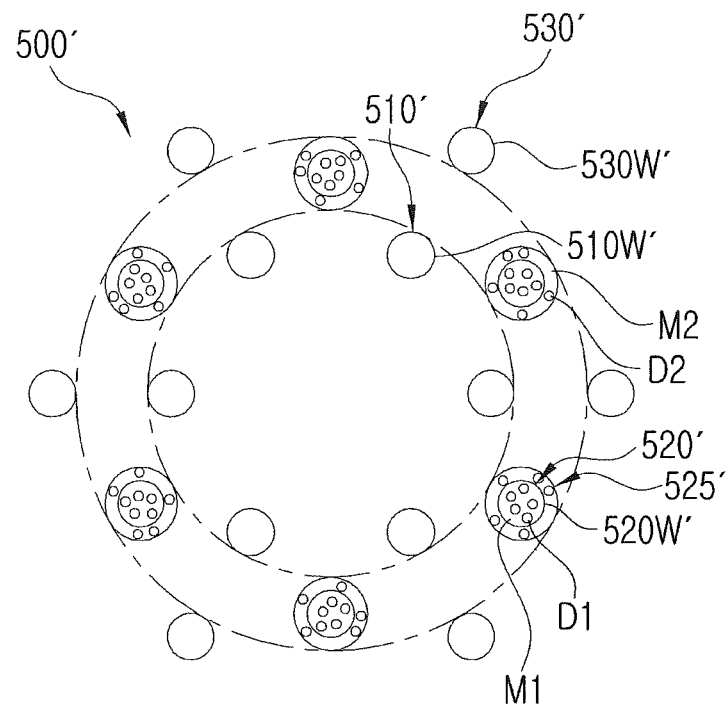
FIG. 7 shows sectional views illustrating sectional structures based on mutual connection configurations between stent structures in the state in which the second stent structure of the drug-releasing biodegradable stent according to the second embodiment of the present invention has been subjected to a coating process.
Figure 7:
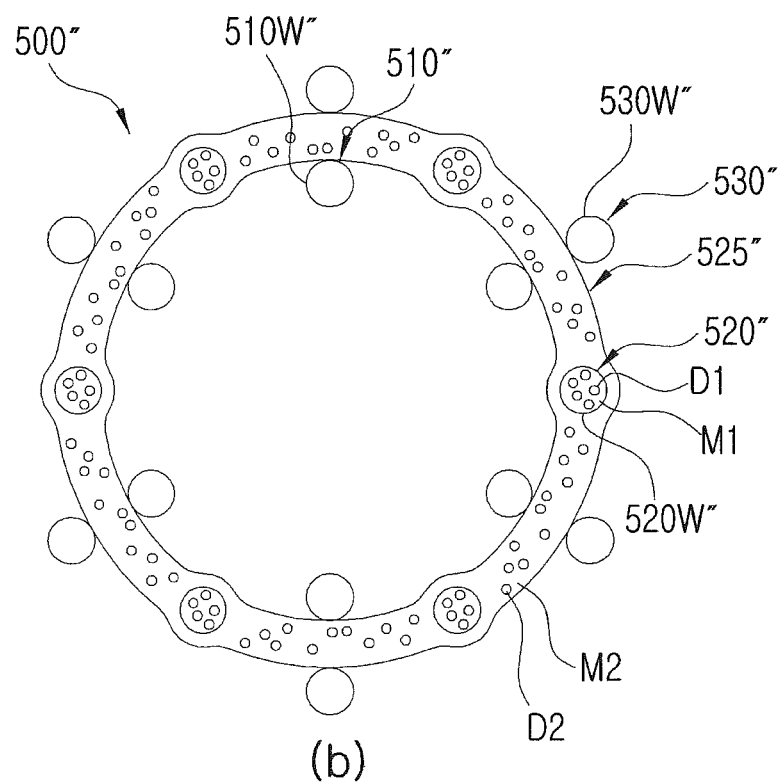

In this case, coating layer formation configurations may be divided into two types, as shown in FIG. 7. First, the sectional structure of a drug-releasing biodegradable stent 500' having a first coating configuration is as shown in FIG. 4(a).

The film-shaped coating layer 525' is formed throughout the overall second stent structure 520' of the drug-releasing biodegradable stent 500' having a first coating configuration through the spraying of a coating mixture or a deposition process in a coating mixture after 3D printing, as shown in FIG. 7(b).

Furthermore, as a result, the cell structure of the second stent structure 520 is blocked by the coating layer 525 constituting a film and forms a tubular shape as a whole, and the first stent structure 510 and the third stent structure 530 are located inside and outside the film-shaped coating layer 525 of the second stent structure 520, respectively.

The coating layer 525" is formed to be placed and applied onto the outside of the surface of a wire structure 520W" constituting the framework of the second stent structure 520" of the drug-releasing biodegradable stent 500" having a second coating configuration through the spraying of a coating mixture or a deposition process in a coating mixture after 3D printing, as shown in FIG. 7(a).

Furthermore, as a result, the cell structure of the second stent structure 520" is merely narrowed but is not blocked by the coating layer 525", and the first stent structure 510 and the third stent structure 530 are located inside and outside the second stent structure 520", around which the coating layer 525" is formed on the wire structure, respectively.

The coating layers 525 and 525", which may be provided in various configurations, as described above, are provided using the coating mixture in which the biodegradable polymer M2 and the drug D2 are mixed together. Descriptions of the embodiments of the biodegradable polymer M2 and the drug D2 used in the coating mixture and the embodiments of the biodegradable polymer M1 and the drug D1 used in the above-described a printing material are the same as the corresponding descriptions given in conjunction with the first embodiment, and thus they will be omitted.

Figure 5:
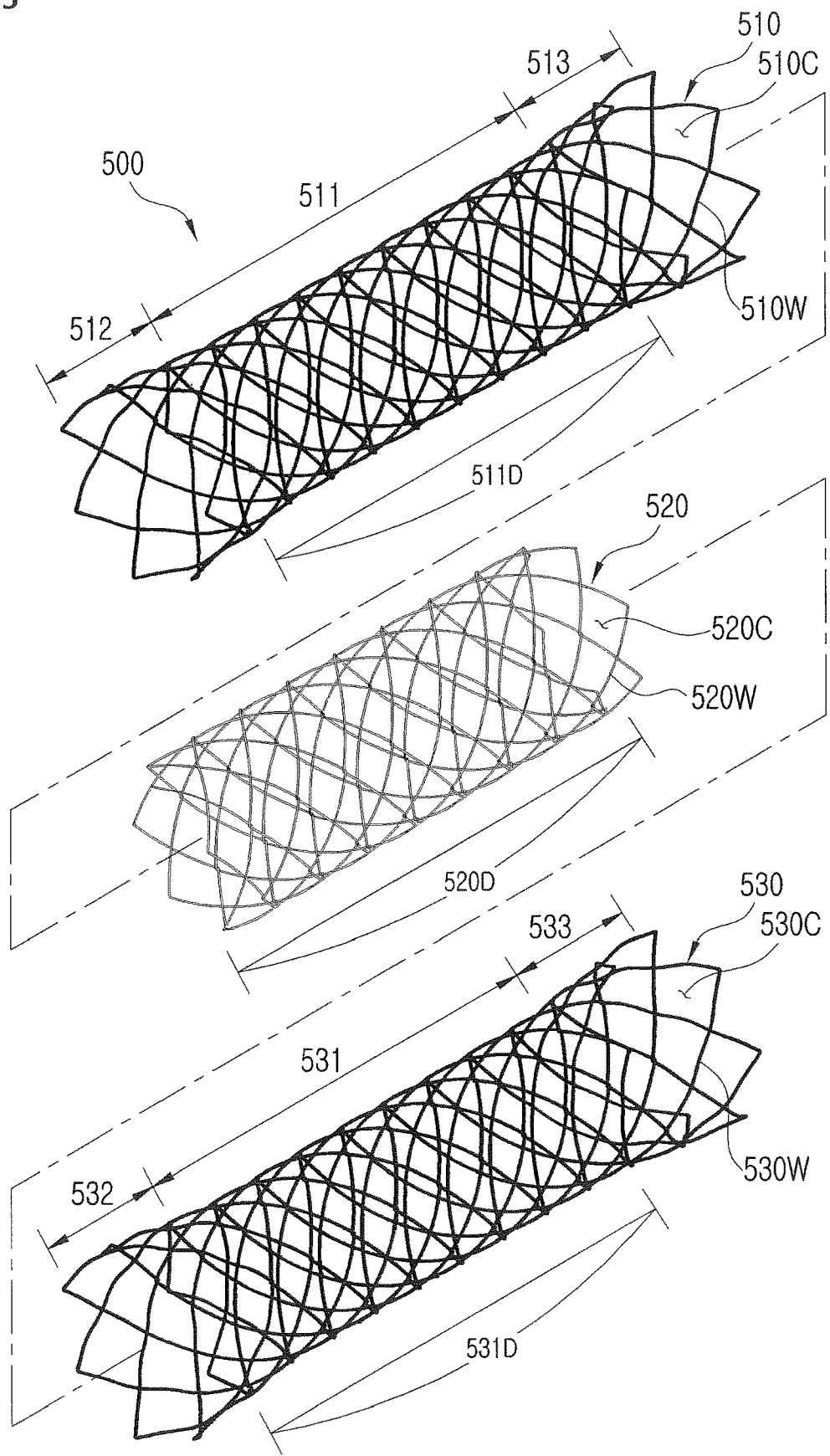
FIG. 5 is an exploded perspective view showing the structure of a drug-releasing biodegradable stent according to a second embodiment of the present invention.

The number of stent structures constituting the overall drug-releasing biodegradable stent 500 is different from that in the first embodiment, as shown in FIG. 5, and thus a mutual connection configuration is also different from that in the first embodiment.

Figure 6:
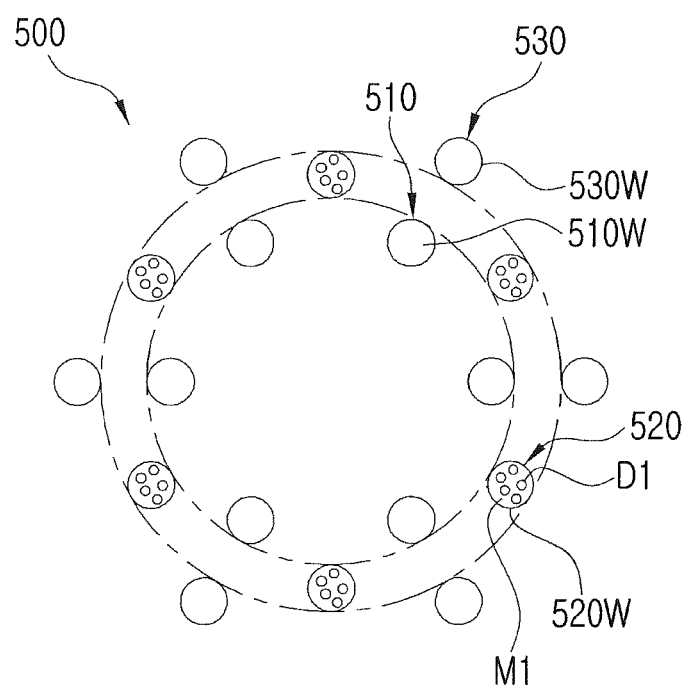
FIG. 6 show sectional views illustrating sectional structures based on mutual connection configurations between the stent structures of the drug-releasing biodegradable stent according to the second embodiment of the present invention.
Figure 8:
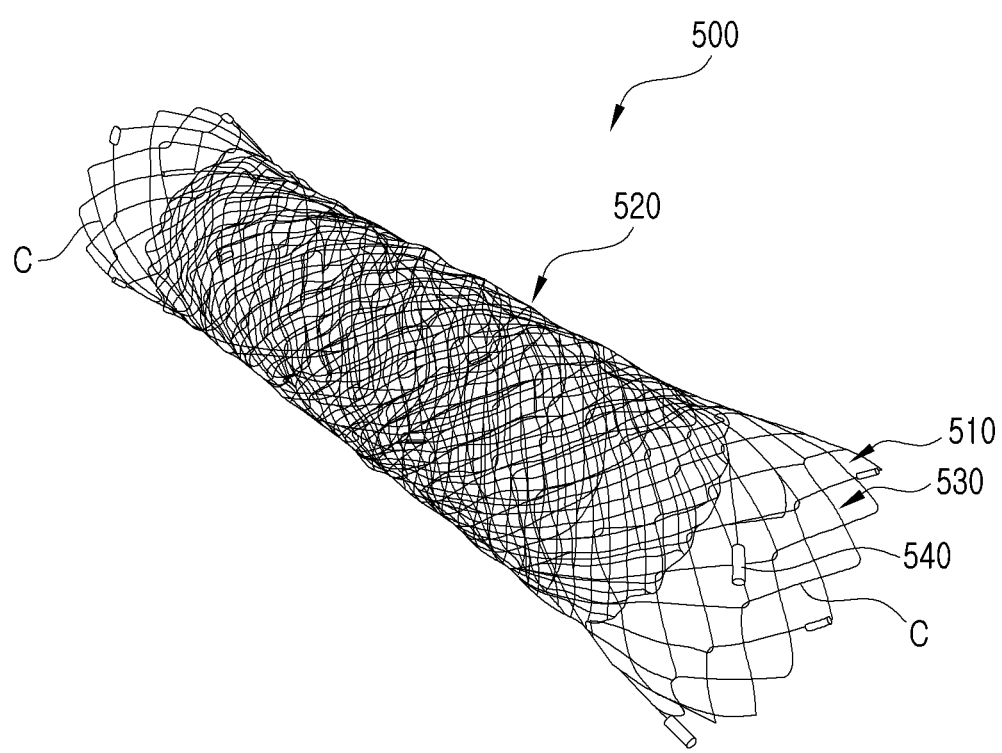
FIG. 8 is a photograph showing the drug-releasing biodegradable stent according to the second embodiment of the present invention.

In connection with this, referring to FIGS. 6 and 8, the third stent structure 530 covers the outer circumferential surface of the first stent structure 510 or the outer circumferential surface of the third stent structure 530 is covered with the first stent structure, and the second stent structure 520 is inserted into and disposed in a space between the first stent structure 510 and the third stent structure 530 that form layers, as described above.

In this case, the third stent structure 530 is provided as a second body portion 531, a third expanded portion 532, and a fourth expanded portion 533 according to their location in an overall structure and their diameter level as the first stent structure 510 is provided as a first body portion 511, a first expanded portion 512, and a second expanded portion 513, as in the first embodiment.

First, the second body portion 531 is the central body portion of the stent that substantially performs the function of restoring a luminal diameter at a stent placement location through the expansion of the third stent structure 530. The second body portion 531 is formed in a hollow cylindrical shape.

Next, the third expanded portion 532 is one end wing portion of the stent that extends from one end of the second body portion 531, that has a larger diameter than the second body portion 531, and that provides the property of preventing the stent from being removed and moved when the stent is placed.

Finally, the fourth expanded portion 533 is the other end wing portion of the stent that extends from the other end of the second body portion 531, that has a larger diameter than the second body portion 531, and that provides the property of preventing the stent from being removed and moved when the stent is placed.

Furthermore, the second stent structure 520 is provided to have the same or a shorter length 520D as and than the first body portion 511 and the second body portion 531, and is preferably inserted and disposed between the first body portion 511 and the second body portion 531.

In other words, the length 520D of the second stent structure 520 is the same as or slightly shorter than the lengths 511D and 513D of the first body portion 511 and the second body portion 531, as shown in FIG. 5.

The reason for this is to allow the drug to be effectively applied to a lesion without being applied to an unnecessary region by taking into account the fact that the first body portion 511 and the second body portion 531 configured to substantially perform the function of restoring a luminal diameter narrowed due to the occurrence of the lesion come into direct contact with the lesion.

In other words, the length 520D of the second stent structure 520 is provided to be the same as or slightly shorter than the length of the first body portion 511 or second body portion 531, and the second stent structure 520 is inserted and disposed between the first body portion 511 and the second body portion 531 and located near a lesion when the stent is placed.

At least one coupling portion C configured to integrate the first expanded portion 512 and the third expanded portion 532 with each other or to integrate the second expanded portion 513 and the fourth expanded portion 533 with each other is provided on each side of the first body portion 511 and the second body portion 531 between which the second stent structure 520 is inserted and disposed.

More specifically, at least one coupling portion C configured to connect the metal wires 510W and 530W in a twisted form or integrate the metal wires 510W and 530W with each other through separate soldering or the installation of a separate member is provided on one side of the first expanded portion 512 of the first stent structure 510 and the third expanded portion 532 of the third stent structure 530. This is also applied to one side of the second expanded portion 513 of the first stent structure 510 and the fourth expanded portion 533 of the third stent structure 530.

In this case, the coupling portions C provided on both ends of the first stent structure 510 and the third stent structure 530, respectively, allow the second stent structure 520 inserted and disposed between the first stent structure 510 and the third stent structure 530 to have predetermined mobility while preventing the second stent structure 520 from being removed from a corresponding placement space.

The reason for this is to overcome the problem in which since the second stent structure 520 is disposed in a fixed state, it is torn or damaged when the drug-releasing biodegradable stent 500 according to the second embodiment is bent in accordance with a luminal structure and, thus, does not have a structural deformation property responsive to bending.

Furthermore, one of the coupling portion C on the one side of the first expanded portion 512 of the first stent structure 510 and the third expanded portion 532 of the third stent structure 530 and the coupling portion C on the one side of the second expanded portion 513 of the first stent structure 510 and the fourth expanded portion 533 of the third stent structure 530 is unwoven or removed when the second stent structure 520 is inserted and released, and thus a space for the insertion and disposition of the second stent structure 520 is opened. After the second stent structure 520 has been inserted and disposed, the unwoven or released coupling portion C is restored back to its original state for integrative coupling.

Accordingly, in the drug-releasing biodegradable stent 500 according to the second embodiment, the plurality of radiopaque markers 540, which are a type of markers used to determine the location of the drug-releasing biodegradable stent 500 within a human body from the outside through inspection using radioactive rays, such as X rays, as shown in FIG. 8, and which perform a location marker function, is disposed in a plurality of portions. It is preferred that a combined connector and radiopaque marker, such as that described in conjunction with the first embodiment, is not disposed.

The embodiments disclosed in the present invention are not intended to limit the technical spirit of the present invention, but are intended to describe it. The scope of the technical spirit of the present invention is not limited by these embodiments. The range of protection of the present invention should be interpreted based on the attached claims, and all technical spirits falling within a range equivalent to the attached claims should be also interpreted as being included in the range of rights of the present invention.

DESCRIPTION OF REFERENCE SYMBOLS 100, 400, 500: drug-releasing biodegradable stent
110, 410, 510: first stent structure
111, 511: first body portion
112, 512: first expanded portion
113, 513: second expanded portion
120, 420, 520: second stent structure
M1: biodegradable polymer in a printing material
D1: drug in a printing material
425, 525: coating layer
M2: biodegradable polymer in coating mixture
D2: drug in coating mixture
130, 540: radiopaque marker
530: third stent structure
531: second body portion
532: third expanded portion
533: fourth expanded portion

The invention claimed is:

1. A drug-releasing biodegradable stent, comprising:
a first stent structure having a plurality of cells defined by a mesh pattern of a woven structure of a metal wire that contains a shape-memory alloy arranged in a specific pattern, the first stent structure having a hollow cylindrical shape;
a second stent structure formed as a 3D print that has a plurality of cells defined by a mesh pattern of a plurality of 3D printed wires containing a printing material including a first biodegradable polymer and a first drug and has a hollow cylindrical shape, wherein the second stent structure encompasses an outer circumferential surface of the first stent structure or is encompassed by the first stent structure; and
a coating layer having a coating mixture in which a second biodegradable polymer and a second drug are mixed together, wherein the coating layer has a tubular shape, and the hollow cylindrical shape of the second stent structure is embedded within the coating layer, such that the plurality of cells of the second stent structure are blocked by the coating layer.

2. The drug-releasing biodegradable stent of claim 1, wherein types and/or composition ratios of the first and second biodegradable polymers differ from each other so that the first biodegradable polymer in the printing material used to prepare the second stent structure through 3D printing has a longer biodegradation period than the second biodegradable polymer in the coating mixture.

3. The drug-releasing biodegradable stent of claim 1, wherein the first drug in the printing material used to prepare the second stent structure through 3D printing and the second drug in the coating mixture are provided as identical type of drugs.

4. The drug-releasing biodegradable stent of claim 1, wherein the first stent structure comprises:
a first body portion formed in a hollow cylindrical shape;
a first expanded portion formed at one end of the first body portion to have a larger diameter than the first body portion; and
a second expanded portion formed at a remaining end of the first body portion to have a larger diameter than the first body portion;
wherein the second stent structure is provided to have an identical or shorter length than the first body portion, and is disposed such that it covers an outer circumferential surface of the first body portion or an outer circumferential surface thereof is covered with the first body portion.

5. The drug-releasing biodegradable stent of claim 4, further comprising a plurality of radiopaque markers disposed at a plurality of portions of the first stent structure in order to ensure visibility of a stent placed in a human body;
wherein at each of both ends of the first body portion is disposed at least one of the plurality of radiopaque markers, the at least one of the plurality of radiopaque markers being disposed to fasten and connect corresponding one of both ends of the second stent structure to the first body portion.

6. A drug-releasing biodegradable stent, comprising:
a first stent structure having a plurality of cells defined by a mesh pattern of a woven structure of a metal wire that contains a shape-memory alloy arranged in a specific pattern, the first stent structure having a hollow cylindrical shape;
a second stent structure formed as a 3D print that has a plurality of cells defined by a mesh pattern of a 3D printed structure containing a printing material including a first biodegradable polymer and a first drug and has a hollow cylindrical shape;
a third stent structure having a plurality of cells defined by a mesh pattern of a woven structure of a metal wire that contains a shape-memory alloy arranged in a specific pattern, the third stent structure having a hollow cylindrical shape, wherein the third stent structure encompasses an outer circumferential surface of the first stent structure or encompassed by the first stent structure; and
a coating layer having a coating mixture in which a second biodegradable polymer and a second drug are mixed together, wherein the coating layer has a tubular shape, and the hollow cylindrical shape of the second stent structure is embedded within the coating layer, such that the plurality of cells of the second stent structure are blocked by the coating layer,
wherein the second stent structure is inserted into and disposed in a space between the first stent structure and the third stent structure.

7. The drug-releasing biodegradable stent of claim 6, wherein types and/or composition ratios of the first and second biodegradable polymers differ from each other so that the first biodegradable polymer in the printing material used to prepare the second stent structure through 3D printing has a longer biodegradation period than the second biodegradable polymer in the coating mixture.

8. The drug-releasing biodegradable stent of claim 6, wherein the first drug in the printing material used to prepare the second stent structure through 3D printing and the second drug in the coating mixture are provided as identical type of drugs.

9. The drug-releasing biodegradable stent of claim 6, wherein:
the first stent structure comprises:
a first body portion formed in a hollow cylindrical shape;
a first expanded portion formed at one end of the first body portion to have a larger diameter than the first body portion; and
a second expanded portion formed at a remaining end of the first body portion to have a larger diameter than the first body portion;
the third stent structure comprises:
a second body portion formed in a hollow cylindrical shape;
a third expanded portion formed at one end of the second body portion to have a larger diameter than the second body portion; and
a fourth expanded portion formed at a remaining end of the second body portion to have a larger diameter than the second body portion; and
the second stent structure is provided to have an identical or shorter length than the first body portion and the second body portion, and is inserted and disposed between the first body portion and the second body portion.

10. The drug-releasing biodegradable stent of claim 9, wherein at least one coupling portion configured to integrate the first expanded portion with the third expanded portion or integrate the second expanded portion with the fourth expanded portion is provided.

11. A drug-releasing biodegradable stent, comprising:
a first stent structure having a plurality of cells defined by a mesh pattern of a woven structure of a metal wire that contains a shape-memory alloy arranged in a specific pattern, the first stent structure having a hollow cylindrical shape;
a second stent structure formed as a 3D print that has a plurality of cells defined by a mesh pattern of a plurality of 3D printed wires containing a printing material including a first biodegradable polymer and a first drug and has a hollow cylindrical shape, wherein the second stent structure encompasses an outer circumferential surface of the first stent structure or is encompassed by the first stent structure; and
a plurality of coating layers, each having a coating mixture in which a second biodegradable polymer and a second drug are mixed together, formed around a surface of each of the plurality of 3D printed wires of the second stent structure such that each of the plurality of 3D printed wires is enclosed by each of the plurality of coating layers, wherein the plurality of cells of the second stent structure are open.

12. The drug-releasing biodegradable stent of claim 11, wherein types and/or composition ratios of the first and second biodegradable polymers differ from each other so that the first biodegradable polymer in the printing material used to prepare the second stent structure through 3D printing has a longer biodegradation period than the second biodegradable polymer in the coating mixture.

13. The drug-releasing biodegradable stent of claim 11, wherein the first drug in the printing material used to prepare the second stent structure through 3D printing and the second drug in the coating mixture are provided as identical type of drugs.

14. The drug-releasing biodegradable stent of claim 11, wherein the first stent structure comprises:
- a first body portion formed in a hollow cylindrical shape;
- a first expanded portion formed at one end of the first body portion to have a larger diameter than the first body portion; and
- a second expanded portion formed at a remaining end of the first body portion to have a larger diameter than the first body portion;
- wherein the second stent structure is provided to have an identical or shorter length than the first body portion, and is disposed such that it covers an outer circumferential surface of the first body portion or an outer circumferential surface thereof is covered with the first body portion.

15. The drug-releasing biodegradable stent of claim 14, further comprising a plurality of radiopaque markers disposed at a plurality of portions of the first stent structure in order to ensure visibility of a stent placed in a human body;
- wherein at each of both ends of the first body portion is disposed at least one of the plurality of radiopaque markers, the at least one of the plurality of radiopaque markers being disposed to fasten and connect corresponding ends of the second stent structure to the first body portion.

\* \* \* \* \*